US008761481B2

(12) United States Patent
Nakano et al.

(10) Patent No.: US 8,761,481 B2
(45) Date of Patent: Jun. 24, 2014

(54) IMAGE PROCESSING APPARATUS FOR PROCESSING TOMOGRAPHIC IMAGE OF SUBJECT'S EYE, IMAGING SYSTEM, METHOD FOR PROCESSING IMAGE, AND RECORDING MEDIUM

(75) Inventors: Yuta Nakano, Tokyo (JP); Akihiro Katayama, Zama (JP)

(73) Assignee: Canon Kabushiki Kaisha, Tokyo (JP)

( * ) Notice: Subject to any disclaimer, the term of this patent is extended or adjusted under 35 U.S.C. 154(b) by 150 days.

(21) Appl. No.: 13/310,489

(22) Filed: Dec. 2, 2011

(65) Prior Publication Data
US 2012/0148130 A1 Jun. 14, 2012

(30) Foreign Application Priority Data

Dec. 9, 2010 (JP) ................................ 2010-275144

(51) Int. Cl.
*G06K 9/00* (2006.01)
*A61B 3/14* (2006.01)
(52) U.S. Cl.
USPC ......................................... 382/131; 351/206
(58) Field of Classification Search
USPC ........... 382/131–132, 312; 434/271; 351/206; 356/479
See application file for complete search history.

(56) References Cited

U.S. PATENT DOCUMENTS

| 6,027,493 | A | * | 2/2000 | Donitzky et al. | 606/4 |
| 6,887,083 | B2 | * | 5/2005 | Umeyama et al. | 434/271 |
| 7,524,061 | B2 | * | 4/2009 | Yan et al. | 351/206 |
| 8,081,808 | B2 | * | 12/2011 | Huang et al. | 382/128 |
| 2007/0195269 | A1 | | 8/2007 | Wei | |
| 2007/0287932 | A1 | | 12/2007 | Huang | |
| 2009/0268159 | A1 | | 10/2009 | Xu | |
| 2010/0202677 | A1 | | 8/2010 | Imamura | |

FOREIGN PATENT DOCUMENTS

| CN | 101400295 A | 4/2009 |
| CN | 101697229 A | 4/2010 |
| JP | 2008-073188 A1 | 4/2008 |
| JP | 2009-523563 A | 6/2009 |

* cited by examiner

*Primary Examiner* — Kanjibhai Patel
(74) *Attorney, Agent, or Firm* — Canon U.S.A., Inc., IP Division

(57) ABSTRACT

An image processing apparatus includes a detection unit configured to detect layers on the retina based on tomographic images of the retina, an acquisition unit configured to acquire a region having a larger curvature of the boundary surface between the retina and the corpus vitreum than a threshold value, and a determination unit configured to determine an optic disc of the retina based on the optical disc including a region where a specific layer is not detected by the detection unit and the region acquired by the acquisition unit.

11 Claims, 15 Drawing Sheets

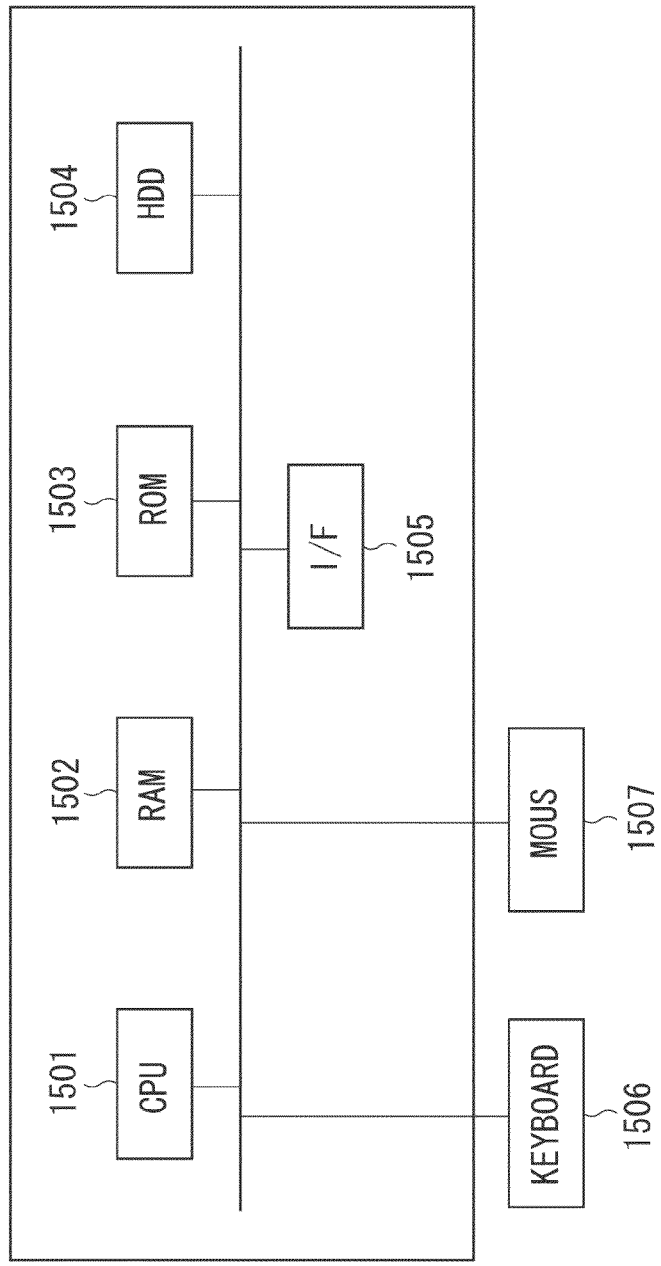

US 8,761,481 B2

IMAGE PROCESSING APPARATUS FOR PROCESSING TOMOGRAPHIC IMAGE OF SUBJECT'S EYE, IMAGING SYSTEM, METHOD FOR PROCESSING IMAGE, AND RECORDING MEDIUM

TECHNICAL FIELD

The present disclosure relates to an image processing apparatus for processing a tomographic image of a subject's eye, an imaging system, a method for processing an image, and a program.

BACKGROUND

An optic disc of a retina is a portion where an optic nerve bundle enters into the deep portion of an eye. Since changes appear at the optic disc in a case of sickness such as glaucoma, it is diagnostically useful to determine the optic disc.

US Patent Application Publication No. 2007/0195269 discusses a technique for determining the optic disc region (also referred to as the "disc region") by acquiring edges of the retinal pigment epithelium which is one of the layers in the retina. This technique is based on an anatomical feature that the retinal pigment epithelium does not exist directly under the vicinity of the optic disc center.

Japanese Patent Application Laid-Open No. 2008-73188 discusses a technique for determining a depression region at the optic disc based on the depth or distance from the anterior ocular segment to the fundus surface. This technique is based on the fact that the optic disc is a depression on the fundus surface.

Meanwhile, when determining the optic disc based on the fact that the retinal pigment epithelium does not exist, false images produced under blood vessels or lesions may make the retinal pigment epithelium unclear. Therefore, a region where the false images are produced may possibly be determined as the optic disc. Further, when determining the optic disc based on the surface shape of the retina, a depression other than the optic disc may possibly be determined as the optic disc.

SUMMARY

According to an aspect of the present invention, an image processing apparatus includes a detection unit configured to detect layers on the retina based on tomographic images of the retina, an acquisition unit configured to acquire a region having a larger curvature of the boundary surface between the retina and the corpus vitreum than a threshold value, and a determination unit configured to determine an optic disc of the retina based on the optical disc including a region where a specific layer is not detected by the detection unit and the region acquired by the acquisition unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 15 illustrates a configuration of an image processing apparatus 1500 according to other exemplary embodiments.

DESCRIPTION OF THE EMBODIMENTS

Various exemplary embodiments, features, and aspects of the invention will be described in detail below with reference to the drawings. Each of the embodiments of the present invention described below can be implemented solely or as a combination of a plurality of the embodiments or features thereof where necessary or where the combination of elements or features from individual embodiments in a single embodiment is beneficial.

Figure 1:
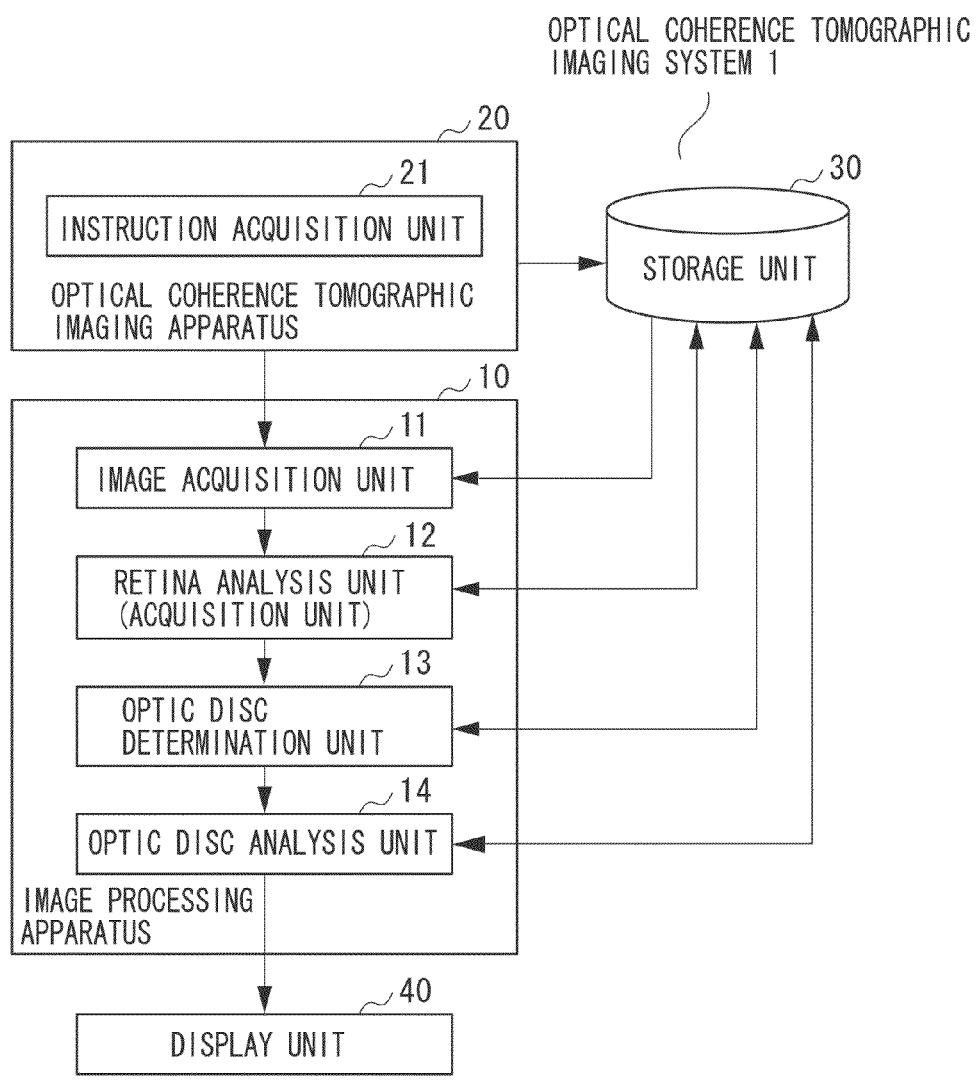
FIG. 1 illustrates a configuration of an optical coherence tomographic imaging system 1.

A configuration of the optical coherence tomographic imaging system 1 according to the present exemplary embodiment will be described below with reference to FIG. 1. With this system, the optical coherence tomographic imaging apparatus 20 captures tomographic images of a subject's eye. The system applies analytical processing to the optic disc on the captured tomographic images, and displays resultant images on a display unit 40.

Figure 6:
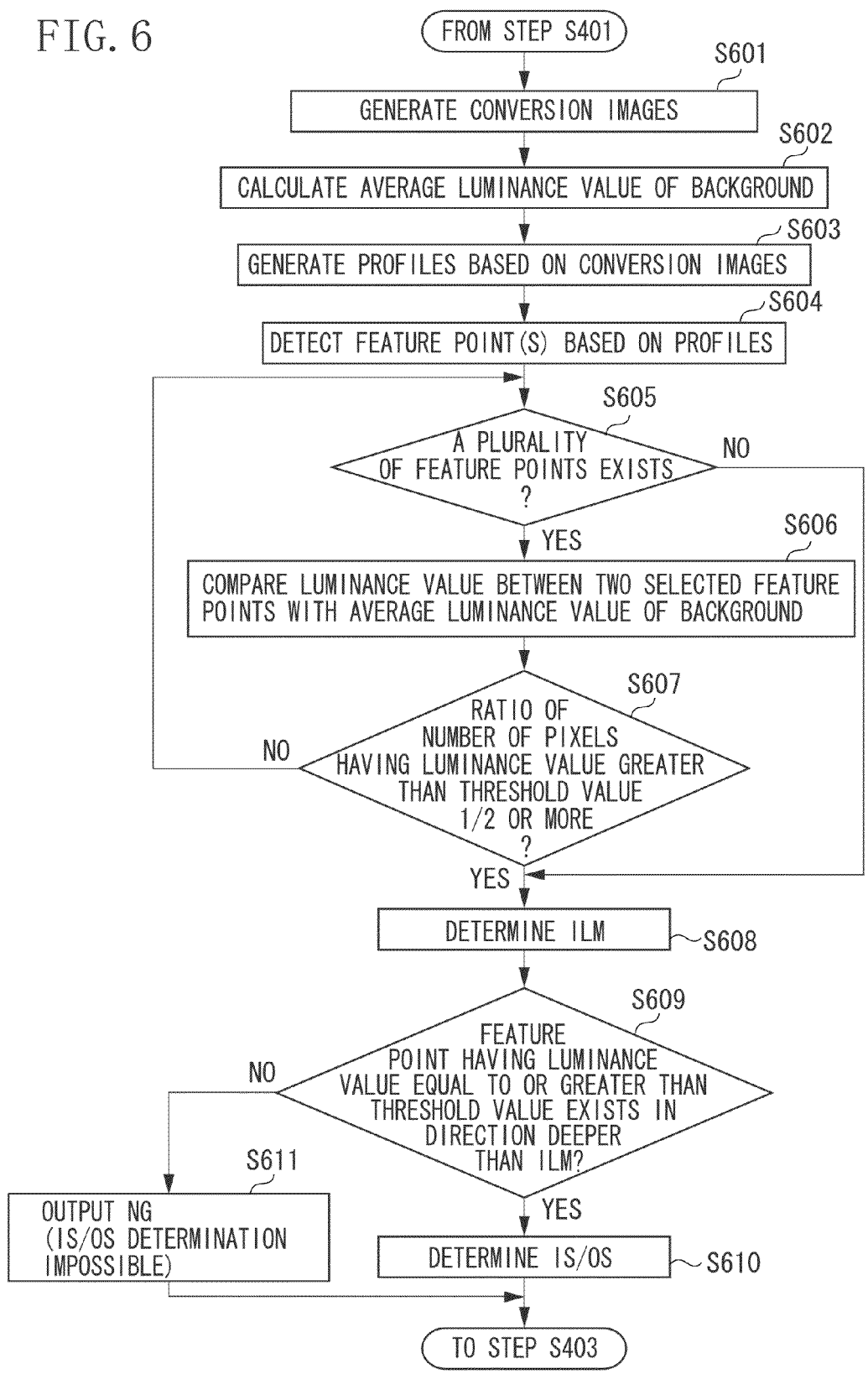
FIG. 6 is a flowchart illustrating processing performed by a retina analysis unit 12.
Figure 9:
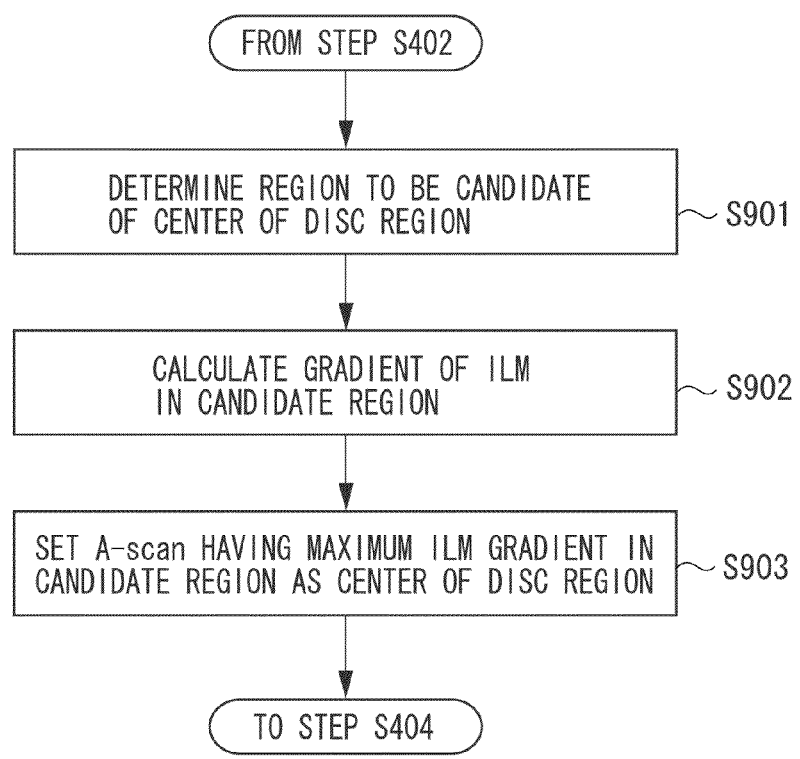
FIG. 9 is a flowchart illustrating processing performed by an optic disc determination unit 13.

The image processing apparatus 10 includes each block illustrated in FIG. 1 as an application-specific integrated circuit (ASIC), a field programmable gate array (FPGA), and other hardware components to enable performing processes illustrated in FIGS. 4, 6, and 9 described below.

The retina analysis unit 12 analyzes the tomographic images captured by the image acquisition unit 11 and determines positions of boundary surfaces between layers of the retina. The retina analysis unit 12 further determines a three-dimensional shape of the ILM and IS/OS. Based on the three-dimensional shape determined based on the tomographic images, the retina analysis unit 12 acquires a depression on the ILM and a region of discontinuous layers at the IS/OS.

The optic disc determination unit 13 determines the optic disc from the tomographic images based on the determined positions of boundary surfaces and the information about the shape of the ILM. The optic disc analysis unit 14 analyzes the optic disc to determine the optic disc region enclosed by the outer edge of the optic disc (this region is also referred to as the optic nerve disc).

Based on the optic disc region, the optic disc analysis unit 14 further determines the optic cup region, which is the disc depression or optic disc depression. The optic disc analysis unit 14 further calculates a cup-to-disc (C/D) ratio and a rim-to-disc (R/D) ratio. The image processing apparatus 10 displays the C/D ratio and the R/D ratio on the display unit 40 together with the tomographic images.

Figure 2:
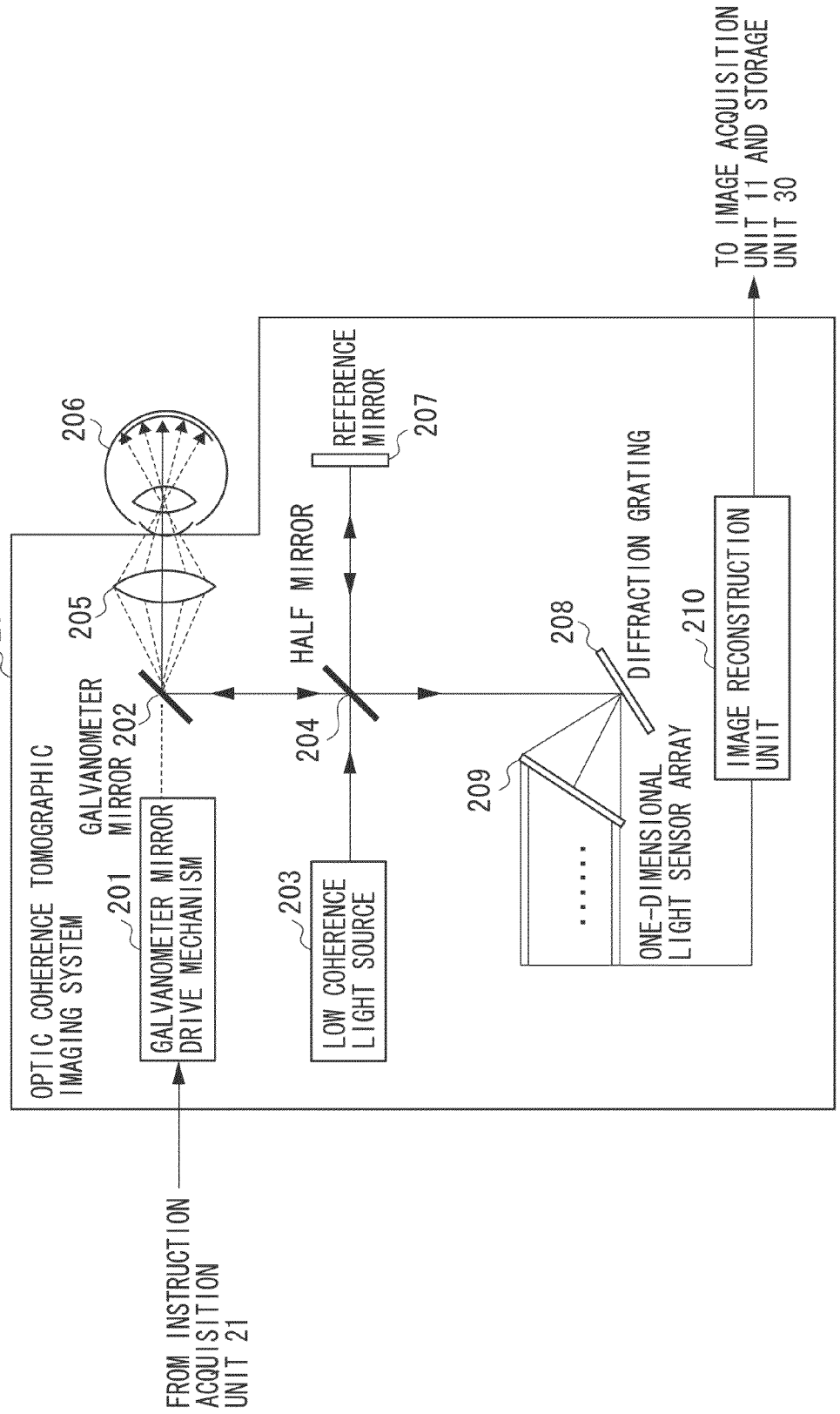
FIG. 2 illustrates a configuration of an optical coherence tomographic imaging apparatus 20.

The configuration of the optical coherence tomographic imaging apparatus 20 will be described below with reference to FIG. 2. The optical coherence tomographic imaging apparatus 20 is an optical coherence tomography (OCT) imaging apparatus based on the principle of the OCT.

An instruction acquisition unit 21 acquires instruction information for adjusting a two-dimensional measurement range and measurement depth for the fundus surface of the subject's eye. Based on the instruction information, a galvanometer mirror drive mechanism 201 drives a galvanometer mirror 202. A half mirror 204 splits light from a low coherence light source 203 into signal light and reference light.

The signal light advances through the galvanometer mirror 202 and an object lens 205, and then is reflected or scattered by a subject's eye 206. The reference light is reflected or scattered by a reference mirror 207, which is fixedly arranged. The half mirror 204 combines the signal light and return light of the reference light to generate interference light.

A diffraction grating 208 spectroscopically decomposes the interference light into wavelength components having a wavelength from λ1 to λn, and detects each wavelength component by using a one-dimensional light sensor array 209. Based on a detection signal of each wavelength component of the interference light output from the one-dimensional light sensor array 209, the image reconstruction unit 210 reconstructs the tomographic images of the retina.

A-scan refers to irradiating an arbitrary position on the fundus with signal light to acquire a one-dimensional image. The one-dimensional image in the depth direction acquired through an A-scan is referred to as A-scan image.

B-scan refers to intermittently irradiating the fundus with signal light along an arbitrary line by using the galvanometer mirror 202 to scan the fundus surface. A tomographic image acquired through B-scan is referred to as B-scan image.

An image intersecting with the A-scan direction based on A-scan images acquired through A-scan at a plurality of positions in a predetermined region on the fundus surface is referred to as a C-scan image.

Figure 3:
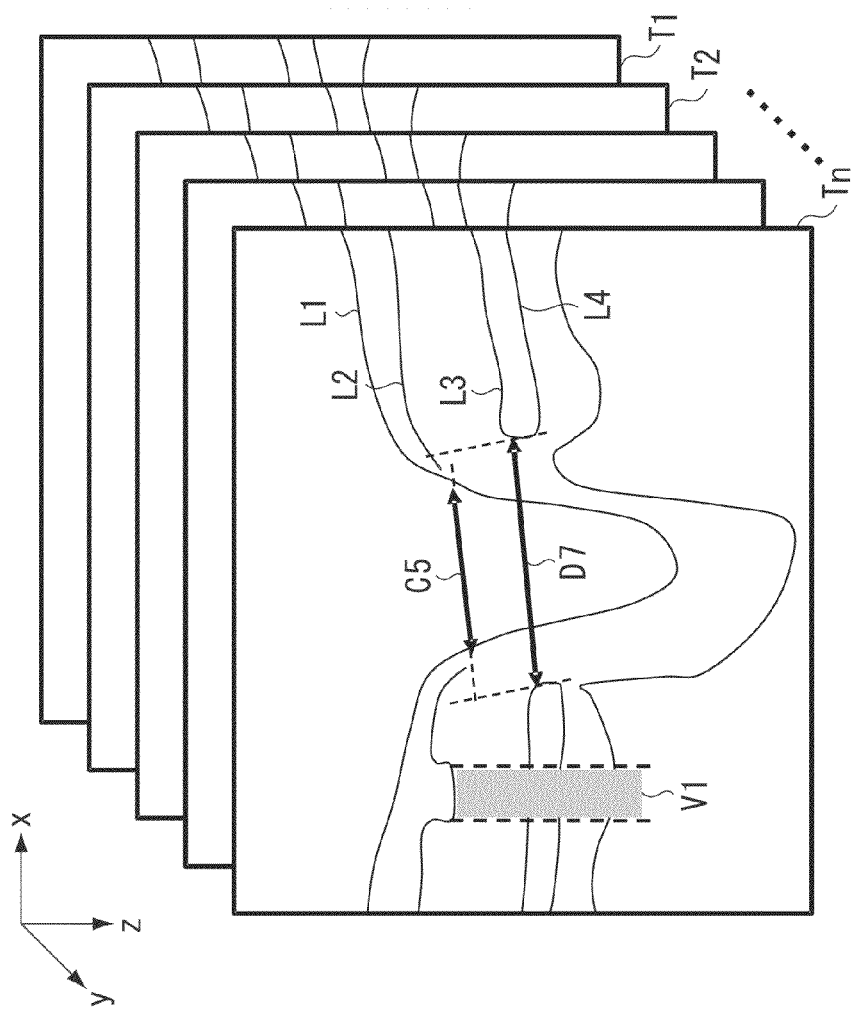
FIG. 3 illustrates exemplary tomographic images of the vicinity of the optic disc.

FIG. 3 illustrates exemplary tomographic images of the vicinity of the optic disc captured by the optical coherence tomographic imaging apparatus 20, i.e., images T1 to Tn acquired by deflecting the signal light to scan the fundus surface along n parallel lines (B-scan). The x-axis direction is a direction in parallel with the B-scan direction, the y-axis direction is a direction along which scan lines are arranged, and the z-axis direction is the depth direction of the eye.

Referring to FIG. 3, a boundary L1 is a boundary between the ILM and the corpus vitreum (hereinafter this boundary is referred to as the ILM boundary), i.e., a boundary between the retina and the corpus vitreum. A boundary L2 is a boundary between the nerve fiber layer (NFL) and a lower layer (hereinafter this boundary is referred to as the NFL boundary). A boundary L3 is a boundary between the IS/OS and an upper layer (hereinafter this boundary is referred to as the IS/OS boundary). A boundary L4 is a boundary between the retinal pigment epithelium (RPE) and a lower layer (hereinafter this boundary is referred to as the RPE boundary).

As illustrated in FIG. 3, the optic disc is featured firstly in that the ILM boundary is depressed and secondly in that neither the IS/OS (IS/OS boundary) nor the RPE (RPE boundary) exists. Based on these two features, the optic disc position is determined based on tomographic images of the retina layer.

It is known that the shape of the ILM boundary largely differs among individuals. With some individuals, the optic disc depression may not be so large, and a depression of the ILM boundary may appear in regions other than the optic disc. However, from the anatomical viewpoint, it is only the optic disc that does not have the RPE except for lesions. Therefore, even if there exists a plurality of depressions, the optic disc position can be accurately determined by determining whether the RPE is present or not.

An effect of using these two features together becomes remarkable in a case where false image regions are produced by blood vessels or lesions. A region v1 is called false image region. A false image region is produced when the signal light of the OCT is absorbed by blood vessels or lesions, and very weak signal light arrives at a position deeper than the blood vessels or the lesion. Existent layers and structures disappear in false image regions.

In many cases where false images are produced by lesions such as bleeding and white spots, the ILM boundary above the lesioned portion is raised toward the side of the corpus vitreum. As a result, the ILM boundary forms a convex portion.

Further, when blood vessels exist, it is rare that the top portion of the blood vessels forms a depression. The present exemplary embodiment determines whether a depression is formed at the ILM boundary to determine the optic disc, thus covering the shortcomings of determining the optic disc position based only on whether the RPE is present or not.

Referring to FIG. 3, a region C5 indicates the optic disc region, and is called an optic disc region. A region D7 indicates a region surrounded by the edge of the optic disc depression. This region is called the optic cup region.

In the present exemplary embodiment, the optic disc region is defined as a region surrounded by RPE edges according to the definition by the patent reference 1. As illustrated in FIG. 3, the optic cup region is defined as a curved surface formed by connecting a certain plane and intersections between the plane and the ILM. The certain plane is formed by vertically moving an RPE edge plane (a plane formed by connecting the RPE edges) upward in parallel by a predetermined distance.

The C/D ratio is defined as a ratio of the diameter of the outer edge of the optic cup region to the diameter of the optic disc region. With a large C/D ratio, i.e., when the depression is large, glaucoma is suspected.

The R/D ratio is defined as a ratio of the width of a rim region to the diameter of the optic disc passing through the width measurement position and the optic disc center. The rim region means a region surrounded by the outer edge of the optic disc region and the outer edge of the optic cup region. With a small R/D ratio, i.e., when the depression region is large with respect to the optic disc region, glaucoma is suspected.

Figure 4:
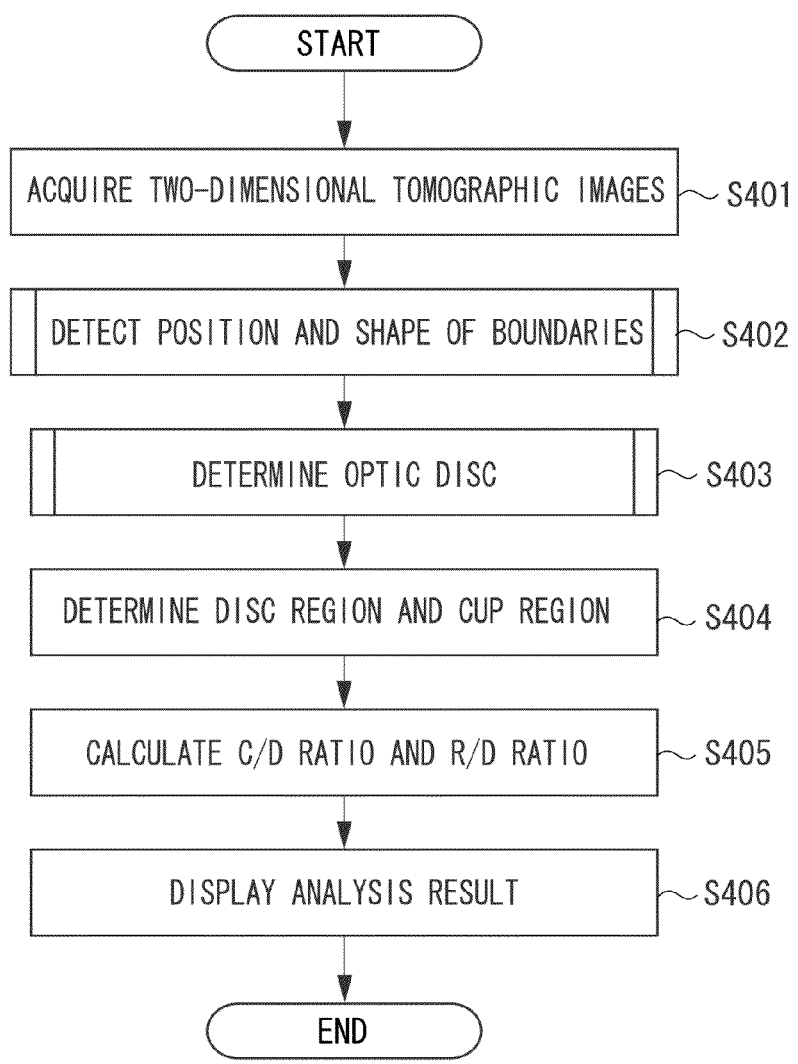
FIG. 4 is a flowchart illustrating processing performed by an image processing apparatus 10.

FIG. 4 is a flowchart illustrating processing in the present exemplary embodiment. Processing performed by the image processing apparatus 10 will be described in detail below with reference to the flowchart.

In step S401, the image acquisition unit 11 acquires a plurality of two-dimensional tomographic images T1 to Tn (FIG. 3) captured by the optical coherence tomographic imaging apparatus 20.

In step S402, for each of the two-dimensional tomographic images T1 to Tn, the retina analysis unit 12 detects the position and shape of the ILM boundary and the IS/OS boundary for each pixel row arranged in the y-axis direction. The processing will be described in detail below in steps S501 to S511 illustrated in FIG. 5.

In step S403, the optic disc determination unit 13 determines as the optic disc a position where the ILM boundary determined by the retina analysis unit 12 has a depressed shape and when the determination of the IS/OS is failed. Based on the depressed shape of the ILM boundary, the optic disc determination unit 13 also determines the center position of the optic disc region. The processing will be described in detail below in steps S601 to S604 illustrated in FIG. 6.

In step S404, the optic disc analysis unit 14 determines the optic disc region through the region growth method based on the position of the determined optic disc, and further determines the optic cup region based on the optic disc region.

Figure 5:
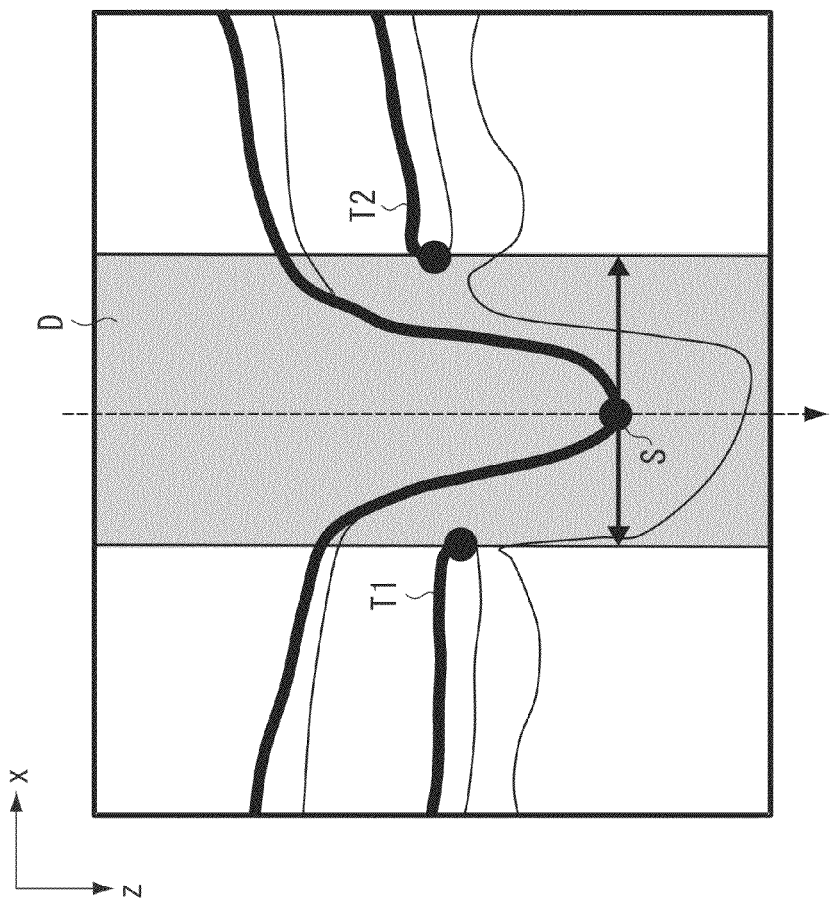
FIG. 5 illustrates optic disc region determination processing performed by an optic disc analysis unit 14.

By using the center of the optic disc region determined in step S403 as abase point, the optic disc analysis unit 14 determines the optic disc region. In the present exemplary embodiment, A-scan having a label "IS/OS determination impossible" is subjected to region growth using A-scan having a label "center of optic disc region" as a seed point S, as illustrated in FIG. 5.

Accordingly, an optic disc region R can be determined by extending it from the inside. Both edges T1 and T2 of the determined optic disc region R can be said to form the RPE edges.

Determining the center of the optic disc region and then determining the optic disc region from the center (inside of the optic disc) in this way enable reducing the influence of false images existing in the retina when determining the optic disc region and the RPE edges.

Thus, the vicinity of the center of the optic disc depression is determined and then the RPE edges are detected from the inside of the optic disc by using the ILM and IS/OS boundary information determined from the images. Therefore, errors in RPE edge determination can be reduced without being affected by false images produced by blood vessels or lesions.

The base point is not necessarily to be the center of the depression, but preferably to be a predetermined position, which is likely to be a region inside the optic disc. However, since the center position of the depression is likely to be a region inside the optic disc, the accuracy in processing for determining the outer edge of the optic disc region can be improved.

In step S405, the optic disc analysis unit 14 calculates the C/D ratio and R/D ratio.

In step S406, the image processing apparatus 10 superimposes the determined RPE edges, optic cup region, and optic disc region onto the tomographic images, and displays resultant images on the display unit 40.

The image processing apparatus 10 also displays the calculated C/D ratio and R/D ratio on the images or other portions. Thus, a relation between the shape of the optic disc depression and the determined optic cup region or optic disc region is clarified. Therefore, based on the images, a user can grasp the shape of the depression and the basis of the calculated C/D ratio and R/D ratio.

As another exemplary embodiment, a two-dimensional region acquired by projecting the optic cup region and the optic disc region onto C-scan images is superimposed onto the C-scan images and then displayed. Thus, the shape of the optic cup region and the optic disc region can be grasped.

The target of superposition is not limited to the C-scan images, but may be a fundus surface image captured by other pieces of modality such as a fundus camera, an integrated image acquired by integrating B-scan images in the depth direction, or a projection image generated by using the B-scan images.

Processing for determining the ILM and IS/OS in step S402 will be described in detail below with reference to FIG. 6. This processing is pre-processing for determining a region where the ILM forms a depression and determining a region on the retina where the IS/OS layer is discontinuous.

In step S601, the retina analysis unit 12 applies image conversion to the OCT tomographic images acquired instep S401 to generate conversion images. In the present exemplary embodiment, the retina analysis unit 12 applies a median filter and a Sobel filter to the tomographic images to generate median images and Sobel images, respectively. In this case, the pixel value increases with high signal intensity and decreases with low signal intensity.

In the present exemplary embodiment, the Sobel filter is provided with such directional features that emphasize the boundary from the lowest to the highest luminance values when viewed from the shallow portion (top portion of image) in A-scan.

The reason is that, to detect a disc, i.e., a portion required for analysis of the optic disc, the present exemplary embodiment utilizes the ILM shape features and the IS/OS boundary information. Therefore, determining the ILM and IS/OS is essential.

With the retina layer structure, the ILM is a boundary between the corpus vitreum having a low luminance value and the retina tissue having a comparatively high luminance value, and the IS/OS contacts a comparatively dark tissue toward the shallow portion. Specifically, the ILM and IS/OS are emphasized more by giving the above-mentioned directional features.

In step S602, the retina analysis unit 12 calculates an average luminance value of the background (corpus vitreum) by using the median images generated in step S601. In the present exemplary embodiment, the retina analysis unit 12 applies the binary processing based on the P-tile method to the median images to determine the background region. Then, the retina analysis unit 12 calculates an average value of the luminance value of the median images in the background region.

With the binary processing based on the P-tile method, a histogram is generated for an image subjected to processing, and the binary processing is performed by using as a threshold value a luminance value (accumulated from the highest or lowest one) at the time it reaches a predetermined ratio P. In the present exemplary embodiment, since an approximate value of the ratio of the retina region in image is known, the retina analysis unit 12 performs the binary processing experimentally assuming that the value of the ratio P is 30% from the highest luminance value, and determines pixels having a luminance value equal to or less than the threshold value as background pixels.

After determining all background pixels, the retina analysis unit 12 calculates an average luminance value of the background with reference to the luminance values of the median images for the background pixels.

In step S603, the retina analysis unit 12 generates profiles based on the conversion images generated in step S601. In the present exemplary embodiment, the retina analysis unit 12 generates profiles based on both the median images and Sobel images for each A-scan. Generating profiles based on the median images gives an effect of preventing noise which becomes problematic particularly in OCT images, and making it easier to grasp the tendency of the luminance value.

Figure 7:
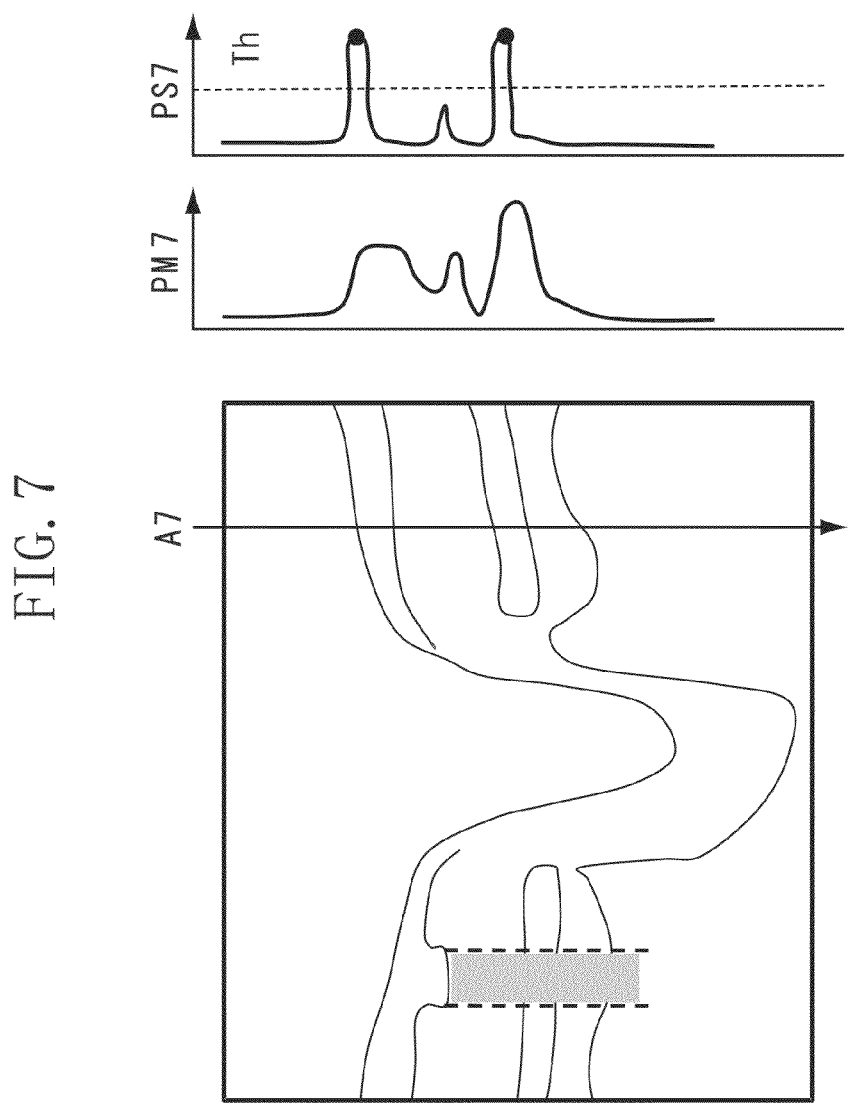
FIG. 7 illustrates an image of the vicinity of the optic disc and A-scan profiles.

Generating profiles based on the Sobel images gives an effect of making it easier to detect candidate points of the retina layer boundary in determining the retina layer boundary to be performed in the latter stage. FIG. 7 illustrates profiles generated based on the median images and Sobel images at an A-scan A7 in a tomographic image. Referring to FIG. 7, the tendency of the luminance value can be seen from a profile PM7 of the median images, and candidate points of the retina layer boundary can be seen from a profile PS7 of the Sobel images.

It is not necessary to generate profiles based on these conversion images, and it is preferable to detect edges having a predetermined intensity from the original images and other conversion images.

In step S604, the retina analysis unit 12 detects local maximum points (hereinafter referred to as peaks) based on the profiles generated in step S603. In the present exemplary embodiment, the retina analysis unit 12 detects peaks in the profiles generated based on the Sobel images. In peak detection, a threshold value determined experimentally or based on image information is used.

On the retina, the ILM and IS/OS reflect and scatter many signals. Therefore, the use of the Sobel filter having such directional features that emphasize the boundary from the lowest to the highest luminance values when viewed from the shallow portion (described in step S601) makes it easier to detect peaks as intense edges.

Since intense edges detected by the Sobel filter having the directional features exists only at lesions (for example, peeling of the corpus vitreum cortex), the ILM and IS/OS can be preferentially extracted by adjusting the threshold value.

In step S605, the retina analysis unit 12 counts the number of peaks detected in step S604 and, based on the number of peaks, determines whether a plurality of feature points exists. In the present exemplary embodiment, when there exists a plurality of peaks not determined as the retina layer boundary or the corpus vitreum cortex (YES in step S605), the retina analysis unit 12 selects in A-scan two peaks from the shallow portion. Then, the retina analysis unit 12 recognizes the two peaks as first and second peaks, and the processing proceeds to step S606. When only one peak exists (NO in step S605), the retina analysis unit 12 recognizes the largest peak as the first peak, and the processing proceeds to step S608.

In step S606, the retina analysis unit 12 compares the average luminance value of the profiles of the median images between the two peaks selected in step S605 with the average luminance value of the background.

In the present exemplary embodiment, for pixels existing between the first and second peaks, the retina analysis unit 12 multiplies the average luminance value of the background calculated in step S602 by a coefficient "1.2", and sets the resultant value as a threshold value. Then, the retina analysis unit 12 counts the number of pixels having a luminance value greater than the threshold value, and calculates the ratio of the acquired number of pixels to the total number of pixels existing between the two peaks.

Although the coefficient is experimentally acquired, the method of the acquisition is not limited thereto. For example, the coefficient may be dynamically determined based on image information by using the ratio of the average luminance value of the background to the average luminance value of non-background regions (regions having a luminance value equal to or greater than the threshold value in the binary processing).

In step S607, based on the ratio calculated in step S606, the retina analysis unit 12 determines whether the ratio of the number of pixels having a luminance value equal to or greater than the threshold value is 1/2 or above. In the present exemplary embodiment, when the calculated ratio is 1/2 or above (YES in step S607), the retina analysis unit 12 determines that the retina tissue exists between the peaks, and the processing proceeds to step S608.

When the calculated rate is less than 1/2 (NO in step S607), the retina analysis unit 12 determines that the background exists between the peaks and therefore does not determine the first peak as a layer boundary (determines it as the corpus vitreum cortex), and the processing returns to step S605 for reselection of two peaks.

Although, in the present exemplary embodiment, the retina analysis unit 12 determines the retina tissue or background based on the ratio of the number of pixels having a luminance value equal to or greater than the threshold value, the method of the determination is not limited thereto. For example, it is also possible to calculate the feature amount based on the profiles, and then make the determination by inputting the calculated feature amount and using a determination device.

In step S608, the retina analysis unit 12 determines one peak as the ILM. In the present exemplary embodiment, the ILM exists at the top end of the retina tissue for the first and second peaks between which the retina tissue is determined to exist in step S607. Therefore, the retina analysis unit 12 determines the first peak as the ILM. In step S608, the retina analysis unit 12 determines the first peak as the ILM also when the processing proceeds to step S608 from step S605.

In step S609, the retina analysis unit 12 determines whether there exists a feature point having a luminance value equal to or greater than the threshold value on the same A-scan at portions deeper than the ILM determined in step S608 (at the bottom portion of image). In the present exemplary embodiment, the retina analysis unit 12 multiplies the magnitude of the ILM peak determined on the same A-scan by a coefficient "0.8", and sets the resultant value as a threshold value. Then, the retina analysis unit 12 determines whether there exists a peak having a luminance value equal to or greater than the threshold value at portions deeper than the ILM.

When a peak exists (YES in step S609), the processing proceeds to step S610. When no peak exists (NO in step S609), the processing proceeds to step S611.

Although the threshold value is experimentally acquired, the method of the acquisition is not limited thereto. For example, the distance between peaks may be used in addition to the magnitude of peak.

In step S610, the retina analysis unit 12 determines as the IS/OS a peak having a luminance value equal to or greater than the threshold value set in step S609. In the present exemplary embodiment, if a plurality of peaks having a luminance value equal to or greater than the threshold value exists, a peak existing at the shallowest position out of peaks having a luminance value equal to or greater than the threshold value is determined as the IS/OS.

In step S611, assuming that the IS/OS determination was not possible, the retina analysis unit 12 attaches a label "IS/OS determination impossible" to A-scan, and the processing ends.

Figure 8:
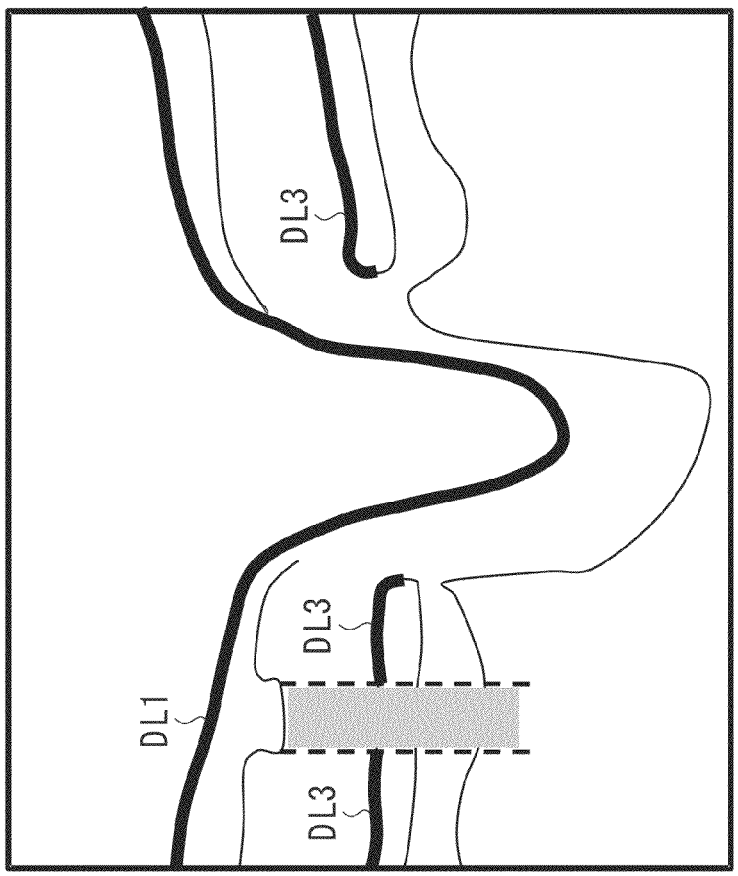
FIG. 8 illustrates the inner limiting membrane (ILM) and the photoreceptor cell inner segment/outer segment junction (IS/OS) determined by the retina analysis unit 12.

Thus, a specific error can be reduced by determining a tissue between the peaks and determining the layer boundary type based on a result of the determination. FIG. 8 illustrates a tomographic image in which the ILM and IS/OS are determined by using this method. Thick solid lines D1 and D3 indicate the determined ILM and IS/OS, respectively.

As illustrated in FIG. 8, the ILM is determined in all A-scans. On the other hand, the IS/OS cannot be determined in some A-scans. As described in step S611, a label "IS/OS determination impossible" is attached to such A-scans.

Since the position of the ILM in the B-scan image is determined, the shape of the ILM can be determined.

The optic disc depression determination processing in step S403 will be described in detail below with reference to FIG. 9.

In steps S901 to S903, the optic disc determination unit 13 determines the center of the optic disc region based on the ILM and IS/OS boundary information determined in step S402. In particular, in step S901, the optic disc determination unit 13 determines a region to be a candidate of the optic disc center (hereinafter referred to as candidate region).

In the present exemplary embodiment, the fact that the IS/OS does not exist in the optic disc region is noticed. The optic disc determination unit 13 sets for each A-scan a local region including a target A-scan and adjacent A-scans. Then, the optic disc determination unit 13 calculates the ratio of A-scan to which a label "IS/OS determination impossible" was attached in step S611 in the local region.

Figure 10:
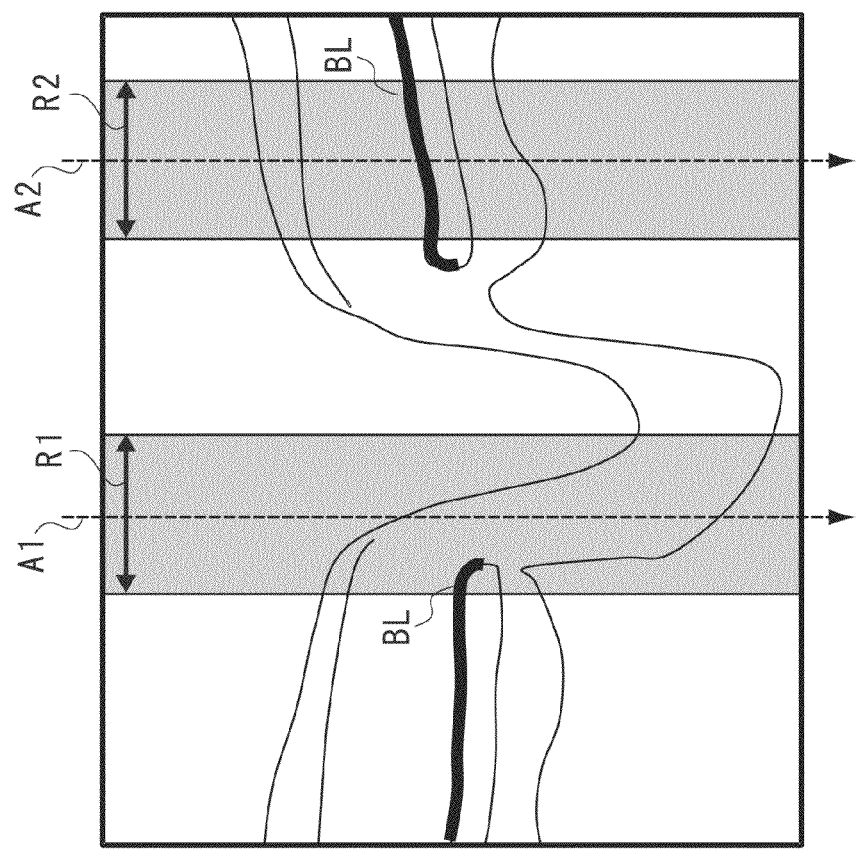
FIG. 10 illustrates processing for determining a region where the IS/OS does not exist.

Specifically, referring to FIG. 10, the optic disc determination unit 13 sets local regions R1 and R2 including target A-scans A1 and A2, respectively, and respective vicinities in a predetermined range. If a label "IS/OS determination impossible" is attached to 1/2 or above of A-scans existing in the local regions, a label "candidate region" is attached to the central A-scan.

For example, referring to FIG. 10, the IS/OS is determined for the A-scan where the IS/OS is illustrated by the thick solid line BL in the local region, and a label "IS/OS determination impossible" is attached to other A-scans.

As illustrated in FIG. 10, since 1/2 or above of A-scans having a label "IS/OS determination impossible" exist in the local region R1, a label "candidate region" is attached to the A-scan A1. On the other hand, since there exists no A-scan having a label "IS/OS determination impossible" in the local region R2, a label "candidate region" is not attached to the A-scan A2.

In step S902, the optic disc determination unit 13 calculates the ILM gradient in the candidate region determined in step S901. In the present exemplary embodiment, the optic disc determination unit 13 sets a local region including a target A-scan and adjacent A-scans, similar to FIG. 11, and performs processing assuming that the A-scan having a label "candidate region" is the center of the local region.

To calculate the gradient, the optic disc determination unit 13 acquires differences between the coordinate value of the ILM at the central A-scan and the coordinate values of the ILM at adjacent A-scans. To acquire the gradient, the optic disc determination unit 13 notices only the component in the vertical direction of an image (the z-coordinate value in FIG. 11) and totals differences between the central A-scan and all of adjacent A-scans assuming that the downward direction is positive.

When the ILM at the central A-scan has a z-coordinate value Ic, and the ILM at adjacent A-scans has z-coordinate values Ii, the gradient is calculated by the following formula (1).

$$\sum_{i=1}^{n}(I_c - I_i) \quad (1)$$

Figure 11:
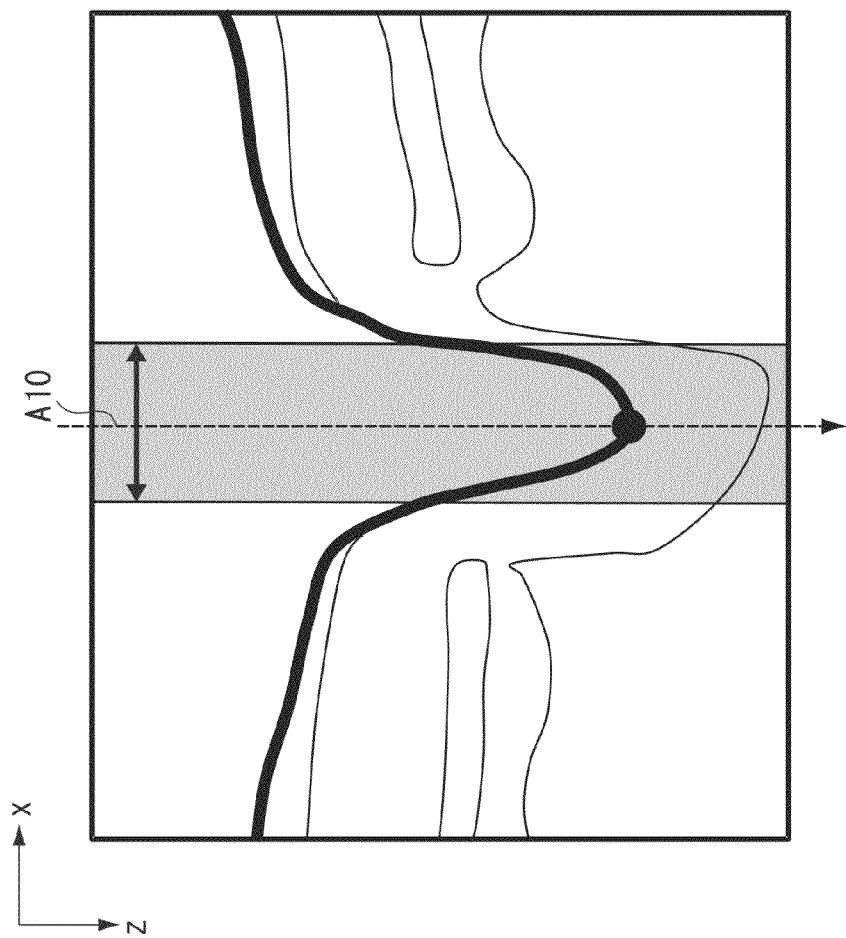
FIG. 11 illustrates processing for determining a center position of a depression region.

The gradient calculated by the formula (1) has a large value when the center of the local region comes in the vicinity of the center of the depression structure of the ILM, as illustrated in FIG. 11.

In step S903, the optic disc determination unit 13 checks the ILM gradient calculated in step S902, and sets an A-scan having the maximum ILM gradient as the center of the optic disc depression. A label "center of optic disc region" is attached to the A-scan set as the center of the optic disc region.

The above-described processing enables determining not only the optic disc position but also the center position of the optic disc region.

With another method, regions having a positive gradient value are determined to the right and left of the central A-scan position to enable determining depression regions on the ILM.

Depression regions and regions where the IS/OS cannot be determined are candidate regions for the optic disc. When only one candidate region exists, the one candidate region is determined as the optic disc region. When a plurality of candidate regions exists, a region having the largest degree of depression, i.e., a region having the maximum gradient value by the formula (1) is determined as the optic disc.

This method also enables determining the optic disc position, and is effective for the retina having few confusing blood vessels or the retina of the normal eye having a flat ILM and few lesions.

Although, in the present exemplary embodiment, the gradient value in the vicinity of a determined position is used as an index for evaluating the degree of curvature, the evaluation index is not limited thereto. It is also possible to use curving states of the boundary surface and the amount of change in the depth direction in a predetermined range at each of a plurality of positions on the boundary surface, the predetermined range including the respective position.

As another exemplary evaluation index, it is also possible to set a reference plane approximated to a curved surface of the ILM by using the least-squares method, etc., and use as an evaluation index a positional difference in the A-scan direction (z-axis direction) between the reference plane and the ILM plane to calculate the degree of depression.

A second exemplary embodiment will be described below based on a case where the region growth method in consideration of the shape of optic disc region is used in step S404 in the first exemplary embodiment. In the vicinity of the optic disc, thick blood vessels gather and therefore many false image regions due to blood vessels exist.

With the optic disc region determination by using the simplified region growth method as in the first exemplary embodiment, a region including false image regions due to blood vessels will be determined as the optic disc region in a case where thick blood vessels are extended from the optic disc. In the present exemplary embodiment, therefore, the "region shape" is added to restriction conditions for the region growth method in step S404 to more accurately determine the optic disc region.

Processing other than the optic disc depression determination processing is common, and duplicated descriptions will be omitted. The apparatus configuration is similar to that of the first exemplary embodiment, and duplicated descriptions will be omitted.

Figure 12:
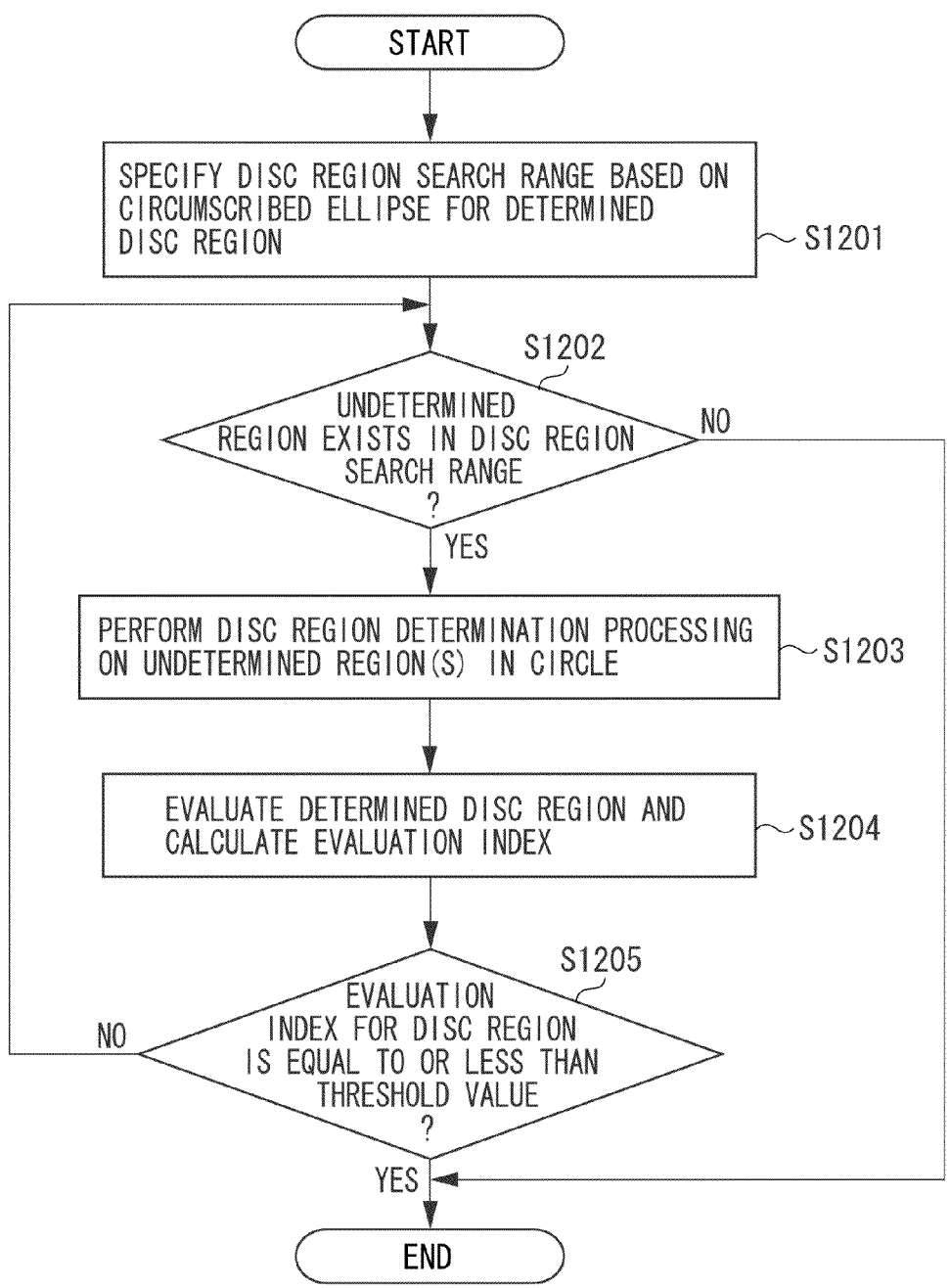
FIG. 12 illustrates the optic disc region determination processing performed by the optic disc analysis unit 14 according to other exemplary embodiments.

The optic disc region and optic cup region determination processing corresponding to step S404 of the first exemplary embodiment will be described in detail below with reference to FIG. 12.

In step S1201, based on the optic disc region determined by the preceding steps, the optic disc determination unit 13 specifies a disc region search range having a predetermined size. In the present exemplary embodiment, the optic disc determination unit 13 assumes an ellipse having a predetermined magnification of a circumscribed ellipse for the determined region, and sets the inside of the ellipse as a disc region search range.

If no optic disc region is determined by the preceding steps, the optic disc determination unit 13 assumes a circle having a predetermined radius centering on the label "center of optic disc region" acquired in step S603, and sets the inside of the circle as a disc region search range.

In step S1202, the optic disc determination unit 13 determines whether there exists a region not having been subjected to the optic disc region determination processing (hereinafter referred to as undetermined region) in the disc region search range specified in step S1201.

The present exemplary embodiment assumes the optic disc region determination processing by the region growth method by using pixels on the profile line of the determined optic disc region as seed points. Therefore, the optic disc determination unit 13 determines whether an undetermined region exists in the vicinity of each seed point on the profile line. When an undetermined region exists (YES in step S1202), the processing proceeds to step S1203. When no undetermined region exists (NO in step S1202), the processing ends.

In step S1203, the optic disc determination unit 13 performs the optic disc region determination processing on undetermined regions. In the present exemplary embodiment, the optic disc determination unit 13 extends the optic disc region based on the region growth method by using pixels on the profile line of the determined optic disc region as seed points. The processing is repeated until no undetermined region remains within the disc region search range specified in step S1201.

In step S1204, the optic disc determination unit 13 evaluates the determined optic disc region, and calculates the evaluation index. In the present exemplary embodiment, the optic disc determination unit 13 evaluates the optic disc region based on the knowledge that the optic disc region is elliptical.

Specifically, the optic disc determination unit 13 acquires a circumscribed ellipse for the determined optic disc region, and calculates the ratio of the area of the ellipse to the area of the determined optic disc region (hereinafter referred to as filling rate) as the evaluation index.

However, the evaluation index for the determined optic disc region is not limited thereto. For example, in the optic disc region determination processing based on the region growth method in step S1203, variation in area and shape of the optic disc region before and after the processing may be used as the evaluation index.

In step S1205, the optic disc determination unit 13 determines whether the evaluation index calculated in step S1204 is equal to or less than a threshold value. In the present exemplary embodiment, the filling rate is acquired as the evaluation index. When the filling rate is equal to or less than the predetermined value (YES in step S1205), the optic disc determination unit 13 assumes that the determined optic disc region is not elliptical, and the repetition of the optic disc region determination processing ends. When the filling rate is greater than the predetermined value (NO in step S1205), the processing returns to step S1201 to repeat the optic disc region determination processing.

By performing the optic disc region determination processing in consideration of the shape of the determined optic disc region in this way, the optic disc region can be accurately determined even if there exists a structure that changes the retina layer structure, such as blood vessels, around the optic disc.

Figure 13:
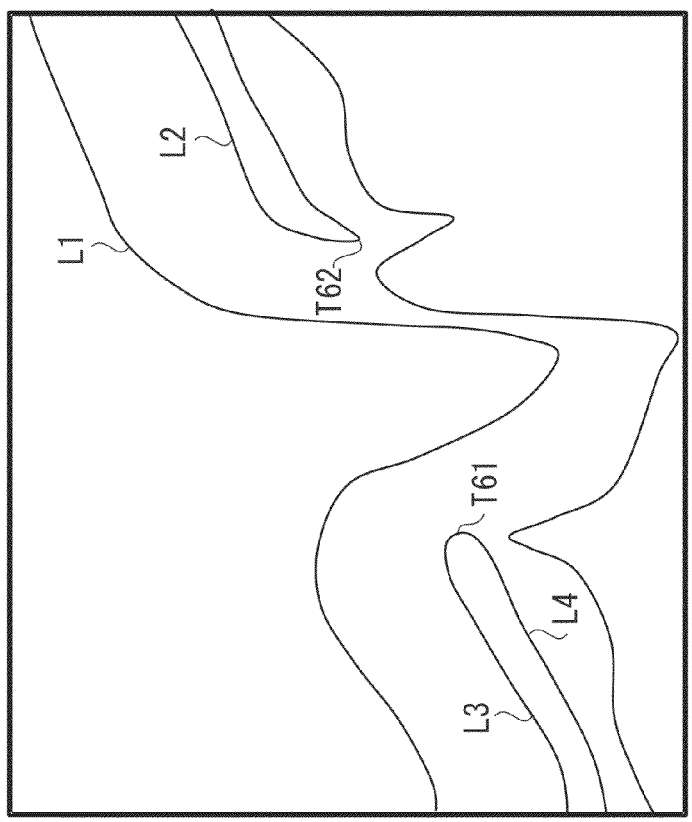
FIG. 13 illustrates a tomographic image of the vicinity of the optic disc when an image of the retina is captured in an inclined way.

A third exemplary embodiment will be described below based on a case where the optic disc region and the RPE edges are more precisely determined through edge component tracing (edge tracing) in step S404 in the first exemplary embodiment. A captured image of the retina may be inclined in a tomographic image, as illustrated in FIG. 13. If the captured image of the retina is inclined, signal levels for portions having a distinguishing structure, such as the RPE edges, may fall.

For example, referring to an RPE edge T62 in FIG. 13, portions closer to the leading end have a lower luminance value, and therefore edge components becomes weaker. Specifically, with this determination method by using a fixed threshold value, RPE edges may be determined to be more outer side of the optic disc region than the actual positions.

In the present exemplary embodiment, accordingly, RPE edge precise extraction processing based on edge tracing is added after step S604 to determine the RPE edges more accurately.

The optic disc determination unit 13 traces edge components from a pre-determined RPE edge toward the inside of the disc region to determine the accurate RPE edge position. In the present exemplary embodiment, the optic disc determination unit 13 checks coordinate values and edge components for each of the determined RPE edges.

Then, the optic disc determination unit 13 traces edges toward the inside of the disc region, starting from each RPE edge position. In edge tracing, the optic disc determination unit 13 updates a search point to a position where edge components existing in the inner vicinity are closest to edge components at each RPE edge position by referring to the edge components at each RPE end, and also updates edge components to be referenced.

The optic disc determination unit 13 repeats this processing to accurately determine the RPE edges and the optic disc region. The processing will be described in detail below in steps S1401 to S1403. Thus, repeating search from the RPE edges once determined in consideration of reduction in luminance due to imaging conditions enables determining the RPE edges more accurately.

Figure 14:
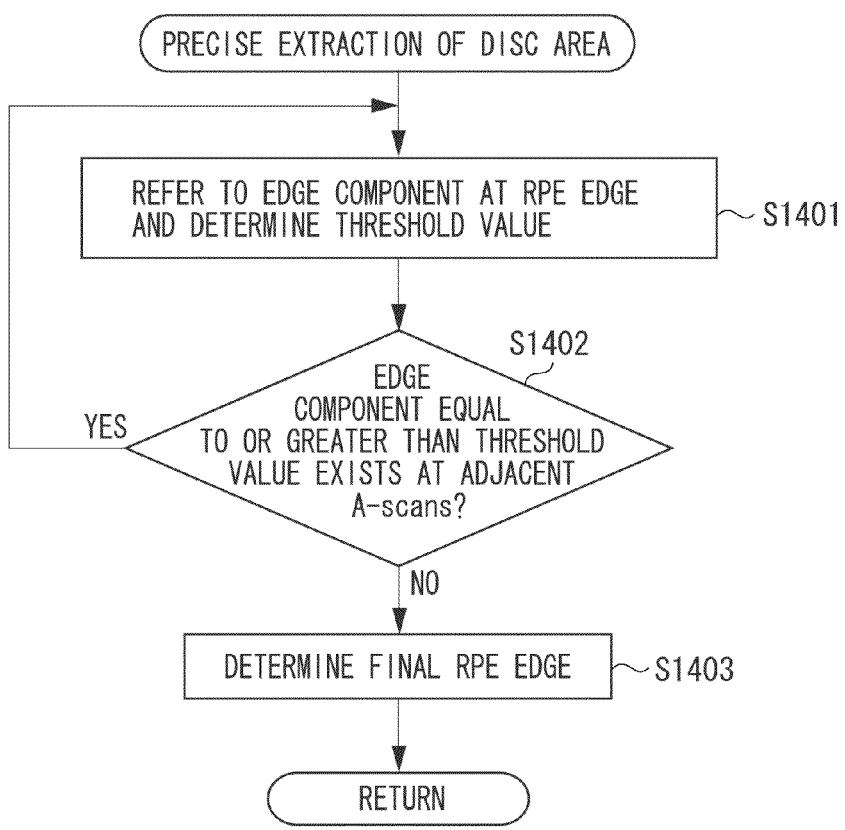
FIG. 14 illustrates the optic disc region determination processing performed by the optic disc analysis unit 14 according to other exemplary embodiments.

The optic disc depression precise extraction processing will be described below with reference to FIG. 14.

In step S1401, the optic disc determination unit 13 determines a threshold value to be used in edge tracing with reference, in the Sobel images, to edge components at the RPE edge position determined in step S402. In the present exemplary embodiment, the optic disc determination unit 13 multiplies the edge components at the RPE edge position by a coefficient "0.3", and sets the resultant value as a threshold value. This coefficient is experimentally acquired and not limited thereto.

In step S1402, by using the threshold value acquired in step S1401 and edge components of the RPE edges, the optic disc determination unit 13 searches, in adjacent A-scans, for pixels having a luminance value equal to or greater than the threshold value and having edge components closest to the edge components at the RPE edge position.

In the present exemplary embodiment, adjacent A-scans refer to A-scans in the B-scan image, which are adjacent toward the inner side of the optic disc from the RPE edges. The optic disc determination unit 13 searches adjacent A-scans for pixels that satisfy the above-mentioned conditions most, within predetermined ranges above and below the RPE at the search start point.

When there exists pixels having a luminance value equal to or greater than the threshold value in the disc region search range (YES in step S1402), the optic disc determination unit 13 updates pixels having a luminance value equal to or greater than the threshold value and having edge components closest to the edge components at the RPE edge position as a new RPE edge, and the processing returns to step S1401. When there exists no pixel having a luminance value equal to or greater than the threshold value (NO in step S1402), the optic disc determination unit 13 does not update the RPE edges, and the processing proceeds to step S1403.

In step S1403, the optic disc determination unit 13 determines the RPE edge determined in step S1402 as a final RPE edge.

Further, when processing the RPE edges as a three-dimensional image, it is also possible to acquire a circumscribed ellipse for the RPE edge determined on the C-scan image plane in consideration of the shape of the optic disc region, and recognize points on the ellipse as a final RPE edge. This gives an effect of correcting the RPE edges shifted by false images due to blood vessels extending from the optic disc region.

Tracing edges based on the edge components and position information in this way enables accurately determining the RPE edges without mistaking them for other retina layer boundaries even in the case of reduction in luminance due to imaging conditions. The above configuration enables more accurately determining the optic disc region even if there exists a region where the IS/OS or RPE cannot be detected because of false images.

Although, in the above-described exemplary embodiments, the optic disc is determined based on the depressed shape of the ILM boundary surface, the boundary surface is not limited thereto but may be the corpus vitreum cortex. In short, it is preferable that, a detection unit detects layers on the retina based on tomographic images of the retina, an acquisition unit acquires a region having a larger curvature on the boundary surface between the retina and the corpus vitreum than a threshold value and a determination determines an optic disc of the retina based on a region where a specific layer is not detected by the detection unit and the region acquired by the acquisition unit.

Although, in the above-mentioned exemplary embodiments, the optic disc is determined by using a region where the IS/OS layer is discontinuous, the layer is not limited thereto. A region where at least any one of the nerve fiber layer (NFL), ganglion cell layer (GCL), inner nuclear layer (INL), inner plexiform layer (IPL), outer plexiform layer (OPL), IS/OS, and layer boundaries therebetween does not exist may be acquired as a region where the above-mentioned layers are discontinuous.

The determination accuracy can be further improved by determining the optic disc on the premise that a plurality of layers or layer boundaries do not exist.

Processes executed by the image processing apparatus 10 may be executed by a plurality of apparatuses in a distributed way to implement an image processing system. Processes executed by a circuit corresponding to one block illustrated in FIG. 1 may be executed by a plurality of circuits or function blocks in a distributed way.

To implement the functions and processes described in the above-mentioned exemplary embodiments through collaboration of computer hardware and software, a hardware configuration illustrated in FIG. 15 can be used. An image processing apparatus 1500 includes a central processing unit (CPU) 1501, a random access memory (RAM) 1502, a read-only memory (ROM) 1503, a hard disk drive (HDD) 1504, and an interface (I/F) 1505. The image processing apparatus 1500 further includes a keyboard 1506 and a mouse 1507 for accepting an input from the user to the image processing apparatus.

Programs for executing the processes illustrated in the flowcharts in FIGS. 4, 6, 9, 12, and 14 are stored in the ROM 1503 or the HDD 1504. The processes illustrated in these flowcharts are implemented when the CPU 1501 loads a relevant program into the RAM 1502 and then executes it.

The image processing apparatus may include a plurality of CPUs each executing processing in a distributed way. To implement the above-described functions, an operating system (OS) operating on a computer partly or entirely executes the actual processing.

A recording medium storing relevant software (programs or program codes) also constitutes the present invention. The recording medium indicates a non-transitory medium including cache and non-volatile memories, but not including intangibles such as electric waves.

The descriptions in the above-described exemplary embodiments are to be considered as preferable examples, and exemplary embodiments are not limited thereto.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-275144 filed Dec. 9, 2010, which is hereby incorporated by reference herein in its entirety.

What is claimed is:

1. An image processing apparatus comprising:
a detection unit configured to detect layers on the retina based on tomographic images of the retina;
a calculation unit configured to calculate for each of a plurality of positions on a boundary surface between the retina and the corpus vitreum an index for indicating the degree of curvature of the boundary surface;
an acquisition unit configured to acquire a region having a largest curvature of the boundary surface by using the index; and
a determination unit configured to determine an optic disc of the retina based on a region where a specific layer is not detected by the detection unit and the region acquired by the acquisition unit,
wherein the index for evaluating the degree of curvature is at least one of a gradient value, and a depth directional variation on the boundary surface in a predetermined range at each of the plurality of positions on the boundary surface, the predetermined range including the respective position.

2. The image processing apparatus according to claim 1, wherein the determination unit determines an outer edge of the optic disc region based on the shape of the curvature found at the determined optical disc.

3. The image processing apparatus according to claim 2, wherein the determination unit determines the outer edge of the optic disc based on the region growth method by using a predetermined position in the optic disc as a base point.

4. The image processing apparatus according to claim 3, wherein the determination unit determines the position of the base point based on the shape of the curvature at the determined optical disc.

5. The image processing apparatus according to claim 4, wherein the determination unit determines the position of the base point based on the center position of the curvature.

6. The image processing apparatus according to claim 1, wherein the detection unit acquires a region where the retinal pigment epithelium does not exist in the tomographic image as a region where the layers are discontinuous, and
   wherein the acquisition unit acquires the region having a larger curvature based on a position where the boundary surface between the retina and the corpus vitreum has a larger curvature than a threshold value.

7. The image processing apparatus according to claim 1, wherein the detection unit acquires a region where at least any one of the NFL (nerve fiber layer), GCL (ganglion cell layer), INL (inner nuclear layer), IPL (inner plexiform layer), OPL (outer plexiform layer), IS/OS (photoreceptor cell inner segment/outer segment junction), and layer boundaries therebetween does not exist as a region where the layers are discontinuous.

8. The image processing apparatus according to claim 7, further comprising:
   a setting unit configured to set a reference plane for the boundary surface,
   wherein the determination unit calculates the degree of depression on the boundary surface based on a positional difference in the depth direction of the eye between the boundary surface and the reference plane.

9. An imaging system comprising:
   the image processing apparatus according to claim 1;
   an OCT imaging apparatus configured to capture an image of a subject's eye to acquire tomographic images of the retina of the eye; and
   a display unit configured to display the determined optic disc on a surface image or projection image of the retina.

10. A method for processing an image, comprising:
    detecting a layer on the retina based on tomographic images of the retina;
    calculating for each of a plurality of positions on a boundary surface between the retina and the corpus vitreum an index for indicating the degree of curvature of the boundary surface;
    acquiring a region having a largest curvature of the boundary surface by using the index; and
    determining the optic disc of the retina based on a region where a specific layer is not detected and the acquired region,
    wherein the index for evaluating the degree of curvature is at least one of a gradient value, and a depth directional variation on the boundary surface in a predetermined range at each of the plurality of positions on the boundary surface, the predetermined range including the respective position.

11. A non-transitory recording medium storing a program for causing a computer to execute instructions comprising:
    an instruction for detecting layers on the retina based on tomographic images of the retina;
    an instruction for calculating for each of a plurality of positions on a boundary surface between the retina and the corpus vitreum an index for indicating the degree of curvature of the boundary surface;
    an instruction for acquiring a region having a largest curvature on the boundary surface by using the index; and
    an instruction for determining the optic disc of the retina based on a region where a specific layer is not detected and the acquired region,
    wherein the index for evaluating the degree of curvature is at least one of a gradient value, and a depth directional variation on the boundary surface in a predetermined range at each of the plurality of positions on the boundary surface, the predetermined range including the respective position.

* * * * *